United States Patent
Ting et al.

(10) Patent No.: US 7,749,749 B2
(45) Date of Patent: Jul. 6, 2010

(54) BIOREACTOR FOR GENERATING UNIFORM SHEAR STRESS DISTRIBUTION

(75) Inventors: Ta-Wei Ting, Taipei (TW); Yu-Lun Chen, Taipei (TW)

(73) Assignee: National Defense University, Chung-Cheng Institute of Technology, Taoyuan (TW)

( * ) Notice: Subject to any disclaimer, the term of this patent is extended or adjusted under 35 U.S.C. 154(b) by 694 days.

(21) Appl. No.: 11/790,317

(22) Filed: Apr. 25, 2007

(65) Prior Publication Data
US 2008/0038816 A1 Feb. 14, 2008

(30) Foreign Application Priority Data
May 18, 2006 (TW) .............................. 95117594 A

(51) Int. Cl.
*C12M 1/00* (2006.01)
(52) U.S. Cl. .............. 435/289.1; 435/305.1; 435/305.2; 422/102
(58) Field of Classification Search ... 435/283.1–317.1; 422/102
See application file for complete search history.

(56) References Cited

U.S. PATENT DOCUMENTS

| 2004/0009583 A1* | 1/2004 | Benn et al. ................ 435/287.2 |
| 2004/0029261 A1* | 2/2004 | Oldfield ................... 435/287.2 |

* cited by examiner

*Primary Examiner*—Jill Warden
*Assistant Examiner*—Jameson Q Ma
(74) *Attorney, Agent, or Firm*—Bacon & Thomas, PLLC

(57) ABSTRACT

The present invention relates to a bioreactor for generating uniform distribution of shear stress, comprising: a cone, having a cone surface with an outline of modified catenary; a container, having a fixed plate at the bottom inside the accommodating space of said container, and said fixed plate comprises a plurality of reservoirs; wherein the cone tip located above the center of said fixed plate is capable of loading culture media into the accommodating space of said container, that is, into the space between the cone surface and the fixed plate. More uniform shear stress can be generated in the culture media to act on the sample in the reservoirs of the fixed plate when the cone rotates and makes the culture media run. The bioreactor of the present invention can be applied to generate uniform shear stress acting on the fixed plate despite the distance between the cone tip and the fixed plate.

8 Claims, 2 Drawing Sheets

BIOREACTOR FOR GENERATING UNIFORM SHEAR STRESS DISTRIBUTION

BACKGROUND OF THE INVENTION

1. Field of the Invention

The present invention relates to a bioreactor for cell culturing, more particularly, to a device with cone-plate structure for cell culturing.

2. Description of Related Art

In general, the cell-culturing devices have been used to study the dynamic response of vascular endothelial cells to the shear stress from the fluid flow. Said cell-culturing devices mainly comprise a cone, a fixed plate and a culture dish placing on the fixed plate; wherein the cone top and a motor are connected to each other in order to drive the rotation of the cone. The distance h between the cone tip and the fixed plate is maintained at a very small value, and several round holes are made on the fixed plate to arrange the culture dishes in where the cells to be cultured can be evenly seeded. When the cells are cultured in the dishes, the height of the solution surface in the culture dishes is equal to the fixed plate surface. The liquid or the culturing solution placed in the cone-plate area is modulated according to the cone tip angle. The bigger the cone tip angle is, the more the solution is needed, and vice versa. Changing the cone tip angle and the rotating speed of said cone will create different intensity of the shear stress, which may affect the cells in the culture dish at the bottom.

As above-mentioned, the structure of prior art comprises the following disadvantages:

1. The structure orientation is performed by contacting the cone tip to the center of the fixed plate. However, the friction will occur when the cone is in the rotation mode with specific angular velocity and the cone tip and the fixed plate contact to each other, and this will result in some inaccuracy of the angular velocity of the cone. The decrease of the rotating speed will cause the cells in the culture dish fail to experience the expected shear stress and the quantity analysis of the cell culturing experiment cannot be accurately performed.

2. The friction will occur when main parts of the cell culturing device, i.e. cone and plate, contact to each other. This will result in the abrasion of the cone tip and thereby the shear stress value will not be the predetermined value. It will also increase the frequency of cone renewal in order to maintain the geometry of the cone with sharp tip and the accuracy of quantity analysis for cell culturing.

3. Several culture dishes are arranged in a small circular area on the fixed plate. The small area occupies around the outer region of fixed plate and is not able to be enlarged to process a cell culturing experiment in a larger scale.

Therefore, it is desirable to provide an improved method to overcome the aforementioned problems.

SUMMARY OF THE INVENTION

In order to improve the disadvantages of the conventional cone-plate structure for cell culturing, the present invention is provided.

The main object of the present invention is to provide a bioreactor for generating uniform distribution of shear stress; wherein the uniformity of the distribution of shear stress acting on the dishes at the bottom is improved by changing the design of the cone shape, and not affected by the distance between the cone tip and the fixed plate.

Another object of the present invention is to provide a bioreactor for generating uniform distribution of shear stress; wherein the uniformity of the distribution of shear stress acting on the dishes at the bottom is improved by designing the best cone shape according to the cone tip angle.

Still another object of the present invention is to provide a bioreactor for generating uniform distribution of shear stress; wherein the area of the fixed plate for arranging the culture dishes can be enlarged in order to process cell culturing experiment in a larger scale.

The present invention provides a bioreactor for generating uniform distribution of shear stress, comprising: a cone, having a cone surface with an outline of modified catenary; a container, having a fixed plate at the bottom inside the accommodating space of said container, and said fixed plate comprises a plurality of reservoirs; wherein the cone tip located above the center of said fixed plate is capable of loading culture media into the accommodating space of said container; and more uniform shear stress than traditional cone design can be generated in the culture media to act on the sample in said reservoirs of the fixed plate when the cone rotates and makes the culture media run. In addition, the bioreactor of the present invention can be applied despite the distance between the spinning cone tip and the fixed plate to generate uniform shear stress acting on the fixed plate, the place for culturing cells.

Other objects, advantages, and novel features of the invention will become more apparent from the following detailed description when taken in conjunction with the accompanying drawings.

DETAILED DESCRIPTION OF THE PREFERRED EMBODIMENT

The present invention provides a novel design of the cone shape, wherein the cone design relates to the distance h between the cone tip and the fixed plate, and h is maintained to avoid the friction occurred in the practical operation. The existence of the fixed distance h will induce the fluctuation of fluid flow in the area between the cone and the plate, and further affect the uniformity of the distribution of shear stress acting on the surface of fixed plate which is also the liquid surface of the culture dish. When the distance between one point on the fixed plate and the center of the fixed plate is extending, the shear stress at said point is increasing. The present invention provides an improved cone with an outline of modified catenary, which is different from the traditional cone with an outline of triangular. Since there is a fixed distance h between the cone tip and the fixed plate, the modified cone shape will be able to enhance the uniformity of the distribution of shear stress acting on the circular area from $r1=0.2 R$ to $r2=0.9 R$, wherein R is the radius of said fixed plate, and r is the distance from the center of said fixed plate. In addition, the enhancement of uniformity of the distribution of the shear stress in the circular area by the new designed cone will not be affected by the distance h and the cone tip angle. In other words, to maintain the uniformity of the distribution of the shear stress, the shape of the cone shapes with an outline of modified catenary will change according to the distances h between the cone tip and the plate and the cone tip angles. Because the novel designed shape of the cone with outline of modified catenary is able to improve the uniformity of the distribution of shear stress on the surface of the fixed plate, constant shear stress will be generated to act on the cells in the culture dishes despite where the dishes are arranged in the circular area of the fixed plate.

Figure 1:
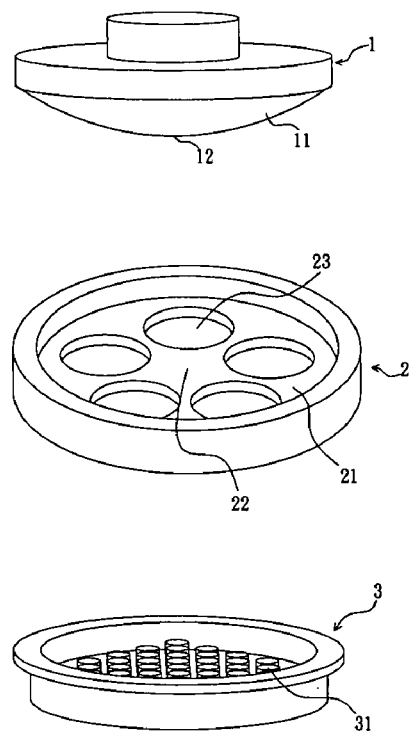
FIG. 1 is a schematic illustration of the members of the bioreactor of the present invention without fabrication.
Figure 2:
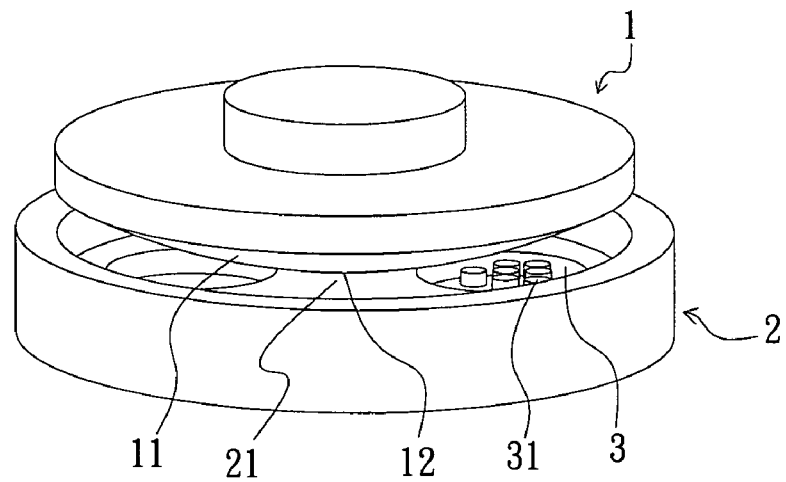
FIG. 2 is a schematic illustration of the bioreactor of the present invention.
Figure 3:
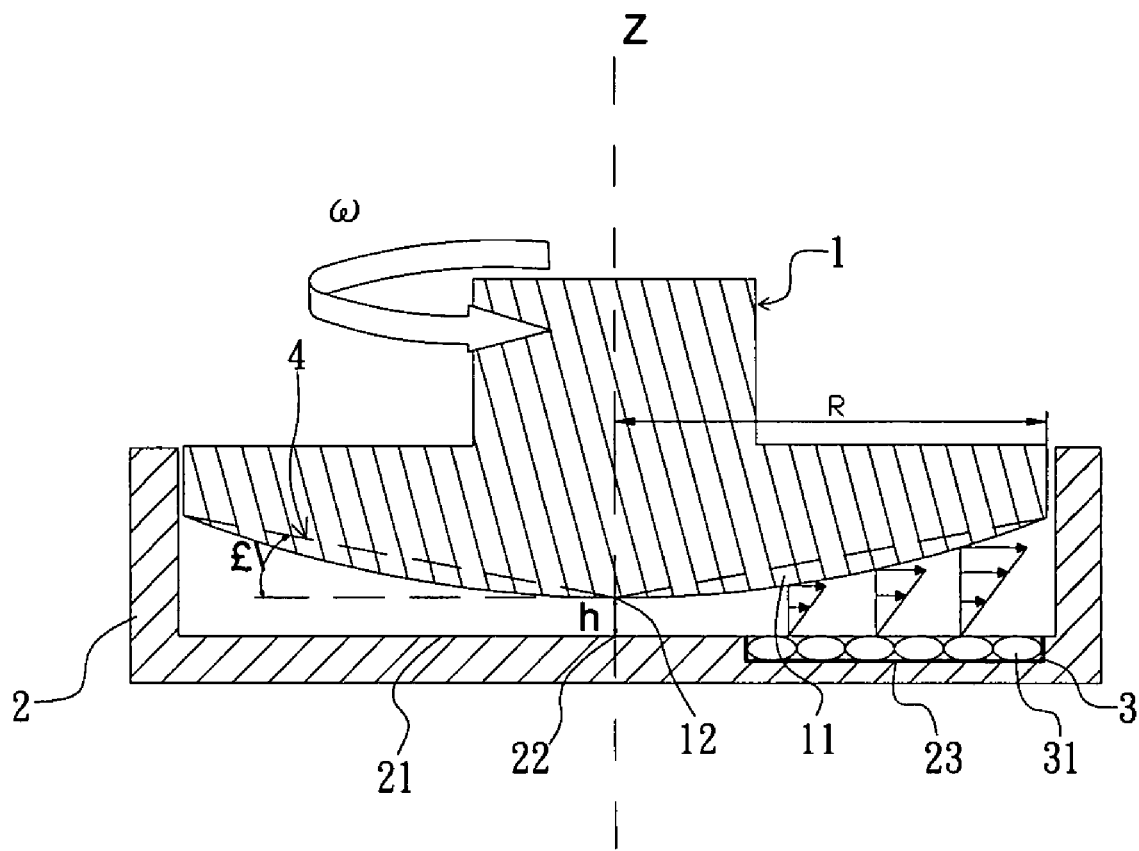
FIG. 3 is a cross-sectional view of the bioreactor of the present invention.

As shown in FIGS. 1, 2 and 3, the bioreactor of the present invention comprises a cone 1, a container 2 and culture dishes 3, wherein:

the cone 1 is novel designed with outline of modified catenary;

the container 2 has a fixed plate 21 located on the bottom of the accommodating space of said container, and the fixed plate 21 comprises a plurality of reservoirs 23 in a circular area from r1=0.2 R to r2=0.9 R for arranging round culture dishes 3 in the reservoirs 23, wherein R is the radius of said fixed plate, and r is the distance from the center 22 of said fixed plate 21;

the culture dishes 3 are round dishes for seeding cell samples 31 inside when doing the experiment or the analysis in associated with cell culturing.

During the fabrication of the device, the cell samples 31 are seeded into the culture dishes 3 first, and then the complete base is set after the culture dishes 3 are arranged in the circular concave reservoirs 23 of the fixed plate 21 and the cone tip 12 of cone 1 is placed at the center 22 of the fixed plate 21; after that, the culture media is loaded into the accommodating space of the container 2 after the culture dishes 3 in the reservoirs 23 of the fixed plate 21 is seeded with cell samples 31, then the cone 1 will rotate around the axis Z and make the culture media run, and uniform shear stress will be generated to act on the cell samples 31.

As shown in FIG. 3, the cone surface 11 of cone 1 with outline of modified catenary is derived from formula (1):

$$Z(r) = \frac{h}{2}\left(e^{\frac{ar^C}{h}} + e^{\frac{-ar^C}{h}}\right) \quad (1)$$

wherein Z(r) is the distance between a point on the fixed plate 21, which located on an imaginary circle whose center point is the center 22 of the fixed plate 21 and its radius is r, and another point on the cone surface 11 right above said point; h is the distance between the cone tip 12 and the fixed plate 21; a is the cone tip angle; C is a constant; and value a is derived from the formula (2) as follow by using the cone radius R, said distance h, and said cone tip angle $\alpha$:

$$a = \frac{h}{R^c} \cdot \ln\left[\frac{H}{h} \pm \sqrt{\left(\frac{H}{h}\right)^2 - 1}\right], \quad (2)$$

wherein $H = h + R \cdot \tan\alpha$.

When C=1, the outline described by formula (1) is a catenary; and when C≠1, the outline described by formula (1) is a modified catenary. Therefore, the Z(r) of formula (1) is determined by said cone radius R, distance h and cone tip angle $\alpha$. In other words, the outline of cone shape described by formula (1) is determined according to those value of R, $\alpha$ and h.

As shown in FIG. 3, when the distance between the cone tip 12 of the cone 1 and the plate 21 is set at a fixed distance, the present invention can generate uniform distribution of shear stress on the fixed plate 21 by changing the outline of cone surface 11 of the cone 1. It is able to decrease the fluctuation of shear stress in the circular area from on the fixed plate 21 from r1=0.2 R to r2=0.9 R, wherein R is the radius of said fixed plate, and r is the distance from the center of said fixed plate. In other words, the fluctuation of shear stress acting on cell sample 31 in culture dishes 3 decreases and the uniformity of the distribution of shear stress in the circular area increases, and the quantitative analysis of cell culturing experiments can be accurately processed by using the bioreactor of the present invention.

Example 1

During the fabrication of the device of the present invention, the cone tip 12 of cone 1 having an outline of improved catenary with $\alpha=1°$ and C=0.643 (solid line) contacts with the center 22 of the fixed plate 21 first, and then raise the cone 1 up by 0.5 mm. After that, the shear stress is evaluated at 100 points evenly scattered in the circular area from r1=0.2 R to r2=0.9 R on the fixed plate 21. The value of shear stress acting on the fixed plate 21 from the cone of the present invention is compared with that from the traditional triangle cone 4 (dashed line) and subjected to statistical analysis. The standard deviation of shear stress reflects that the greater the standard deviation of shear stress is, the greater the fluctuation of shear stress is; which means that the distribution of shear stress is not uniform on the fixed plate 21. On the contrary, the smaller the standard deviation of shear stress is, the smaller the fluctuation of shear stress is; which means that the distribution of shear stress is uniform on the fixed plate 21. In Table 1, it shows the standard deviations of shear stress generated by two different cones 1 and 4 at various rotating angular velocities ($\omega$). It also shows that the distribution of shear stress on the fixed plate 21 by using cone 1 is more uniform than that by using cone 4 despite the rotating angular velocity ($\omega$).

TABLE 1

| h = 0.5 mm, $\alpha$ = 1°, C = 0.643 | | | | |
|---|---|---|---|---|
| | $\omega$ = 1 | $\omega$ = 5 | $\omega$ = 10 | $\omega$ = 15 |
| Standard deviation derived by using the traditional triangle cone | 5.755 | 27.967 | 54.270 | 93.198 |
| Standard deviation derived by using the cone of the present invention | 5.213 | 25.088 | 46.967 | 71.633 |

Example 2

During the fabrication of the device of the present invention, the cone tip 12 of cone 1 having an outline of improved catenary with $\alpha=2°$ and C=0.495 (solid line) contacts with the center 22 of the fixed plate 21 first, and then raise the cone 1 up by 0.5 mm. After that, the shear stress is evaluated at 100 points evenly scattered in the circular area from r1=0.2 R to r2=0.9 R on the fixed plate 21. The value of shear stress acting on the fixed plate 21 from the cone of the present invention is compared with that from the traditional triangle cone 4 (dashed line) and subjected to statistical analysis. The standard deviation of shear stress reflects that the greater the standard deviation is, the greater the fluctuation of shear stress is; which means that the distribution of shear stress is not uniform on the fixed plate 21. In Table 2, it shows the standard deviations of shear stress generated by two different cones 1 and 4 at various rotating angular velocities ($\omega$). It also shows that the distribution of shear stress on the fixed plate 21 by using cone 1 is more uniform than that by using cone 4 despite the rotating angular velocity ($\omega$).

TABLE 2

$h = 0.5$ mm, $\alpha = 2°$, $C = 0.495$

|  | $\omega = 1$ | $\omega = 5$ | $\omega = 10$ | $\omega = 15$ |
|---|---|---|---|---|
| Standard deviation derived by using the traditional triangle cone | 2.393 | 12.533 | 67.051 | 167.898 |
| Standard deviation derived by using the cone of the present invention | 1.941 | 8.717 | 49.814 | 137.793 |

Example 3

During the fabrication of the device of the present invention, the cone tip 12 of cone 1 having an outline of improved catenary with $\alpha=3°$ and $C=0.429$ (solid line) contacts with the center 22 of fixed plate 21 first, and then raise the cone 1 up by 0.5 mm. After that, the shear stress is evaluated at 100 points evenly scattered in the circular area from r1=0.2 R to r2=0.9 R on the fixed plate 21. The value of shear stress acting on the fixed plate 21 from the cone of the present invention is compared with that from the traditional triangle cone 4 (dashed line) and subjected to statistical analysis. In Table 3, it shows the standard deviations of the shear stress generated by two different cones 1 and 4 at various rotating angular velocities ($\omega$). It also shows that the distribution of shear stress on the fixed plate 21 by using cone 1 is more uniform than that by using cone 4 despite the rotating angular velocity ($\omega$).

TABLE 3

$h = 0.5$ mm, $\alpha = 3°$, $C = 0.429$

|  | $\omega = 1$ | $\omega = 5$ | $\omega = 10$ | $\omega = 15$ |
|---|---|---|---|---|
| Standard deviation derived by using the traditional triangle cone | 1.242 | 20.928 | 97.583 | 202.419 |
| Standard deviation derived by using the cone of the present invention | 0.999 | 15.710 | 85.344 | 187.605 |

Example 4

During the fabrication of the device of the present invention, the cone tip 12 of cone 1 having an outline of improved catenary with $\alpha=1°$ and $C=0.444$ (solid line) contacts with the center 22 of the fixed plate 21 first, and then raise the cone 1 up by 0.2 mm. After that, the shear stress is evaluated at 100 points evenly scattered in the circular area from r1=0.2 R to r2=0.9 R on the fixed plate 21. The value of shear stress acting on the fixed plate 21 from the cone of the present invention is compared with that from the traditional triangle cone 4 (dashed line) and subjected to statistical analysis. In Table 4, it shows the standard deviations of shear stress generated by two different cones 1 and 4 at various rotating angular velocities ($\omega$). It also shows that the distribution of shear stress on the fixed plate 21 by using cone 1 is more uniform than that by using cone 4 despite the rotating angular velocity ($\omega$).

TABLE 4

$h = 0.2$ mm, $\alpha = 1°$, $C = 0.444$

|  | $\omega = 1$ | $\omega = 5$ | $\omega = 10$ | $\omega = 15$ |
|---|---|---|---|---|
| Standard deviation derived by using the traditional triangle cone | 4.454 | 21.549 | 40.482 | 58.086 |
| Standard deviation derived by using the cone of the present invention | 3.707 | 17.940 | 33.806 | 47.698 |

Example 5

During the fabrication of the device of the present invention, the cone tip 12 of cone 1 having an outline of improved catenary with $\alpha=1°$ and $C=0.359$ (solid line) contacts with the center 22 of the fixed plate 21 first, and then raise the cone 1 up by 0.1 mm. After that, the shear stress is evaluated at 100 points evenly scattered in the circular area from r1=0.2 R to r2=0.9 R on the fixed plate 21. The value of shear stress acting on the fixed plate 21 from the cone of the present invention is compared with that from the traditional triangle cone 4 (dashed line) and subjected to statistical analysis. In Table 4, it shows the standard deviations of shear stress generated by two different cones 1 and 4 at various rotating angular velocities ($\omega$). It also shows that the distribution of shear stress on the fixed plate 21 is more uniform than that by using cone 4 despite the rotating angular velocity ($\omega$).

TABLE 5

$h = 0.1$ mm, $\alpha = 1°$, $C = 0.359$

|  | $\omega = 1$ | $\omega = 5$ | $\omega = 10$ | $\omega = 15$ |
|---|---|---|---|---|
| Standard deviation derived by using the traditional triangle cone | 2.984 | 14.256 | 26.057 | 35.390 |
| Standard deviation derived by using the cone of the present invention | 2.581 | 12.518 | 23.942 | 34.718 |

The present invention provides a novel bioreactor for cell culturing, comprising: a cone, having a cone surface with an outline of modified catenary; a container, having a fixed plate at the bottom inside the accommodating space of said container, and said fixed plate comprises a plurality of reservoirs. When the fixed distance h between the cone tip and the fixed plate is maintained, the advantages as follow will be obtained:

1. The friction between the cone tip and the fixed plate will not occur during the rotation of the cone; therefore, the cone of the present invention is able to reach the predetermined rotating velocity.

2. The bioreactor with present invention can decrease the fluctuation of the distribution of shear stress on the fixed plate. Therefore, the shear stress acting on the cell samples in the culture dishes is uniform no matter where the culture dishes are arranged on the fixed plate.

3. The cone having an outline of improved catenary, which is designed according to the present invention, can achieve the uniformity of the distribution of shear stress on the fixed plate despite the distance between the cone and the fixed plate and the cone tip angle.

4. The area for arranging the culture dishes on the fixed plate can be enlarged to process a cell culturing experiment in a larger scale.

It should be understood that the embodiments explained herein is only for description. Many other possible modifications and variations can be made without departing from the spirit and scope of the invention as hereinafter claimed by those skilled in the art, and all such modifications and variations are still included in the scope of the present invention.

What is claimed is:

1. A bioreactor for generating uniform distribution of shear stress, comprising:
   a cone, having a cone surface with an outline of modified catenary;
   a container, having a fixed plate at the bottom inside the accommodating space of said container, and said fixed plate comprises a plurality of reservoirs;
   wherein the cone tip located above the center of said fixed plate is capable of loading culture media into the accommodating space of said container; and more uniform shear stress can generate in the culture media to act on the sample in said reservoirs of the fixed plate when the cone rotates and makes the culture media run;
   wherein the outline of said cone surface is derived from the following formulas (1) and (2):

$$Z(r) = \frac{h}{2}\left(e^{\frac{ar^C}{h}} + e^{\frac{-ar^C}{h}}\right) \quad (1)$$

wherein Z(r) is the distance between a point on said fixed plate,
   which located on an imaginary circle whose center point is the center of said fixed plate and its radius is r, and another point on said cone surface right above said point; h is the distance between the cone tip and the fixed plate when the cone is placed in the center of the fixed plate; α is the cone tip angle; C is a constant and C≠1; value a is derived from the formula (2) as follow by using the cone radius R, said distance h, and said cone tip angle α:

$$a = \frac{h}{R^C} \cdot \ln\left[\frac{H}{h} \pm \sqrt{\left(\frac{H}{h}\right)^2 - 1}\right], \quad (2)$$

wherein $H = h + R \cdot \tan\alpha$.

2. The bioreactor according to claim 1, wherein the outline of said cone surface is determined by the distance between said fixed plate and said cone tip, and the cone tip angle and the cone radius of said cone, when the cone is placed in the center of the fixed plate.

3. The bioreactor according to claim 1, wherein the radius of said fixed plate is R, the distance from the center of said fixed plate is r, and said plurality of reservoirs are comprised in the circular area from r1=0.2 R to r2=0.9 R.

4. The bioreactor according to claim 3, wherein said reservoirs having a shape of circular concave.

5. The bioreactor according to claims 1, further comprising at least one culture dish located in said reservoirs of the fixed plate, and cell samples to be tested will be placed inside said culture dish.

6. The bioreactor according to claim 2, further comprising at least one culture dish located in said reservoirs of the fixed plate, and cell samples to be tested will be placed inside said culture dish.

7. The bioreactor according to claim 3, further comprising at least one culture dish located in said reservoirs of the fixed plate, and cell samples to be tested will be placed inside said culture dish.

8. The bioreactor according to claim 4, further comprising at least one culture dish located in said reservoirs of the fixed plate, and cell samples to be tested will be placed inside said culture dish.

* * * * *